US006984774B1

(12) United States Patent
Peterson et al.

(10) Patent No.: US 6,984,774 B1
(45) Date of Patent: Jan. 10, 2006

(54) METHOD AND MATERIALS TO INDUCE RECOMBINATION IN PLANTS

(75) Inventors: Thomas A. Peterson, Ames, IA (US); Yongli Xiao, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 508 days.

(21) Appl. No.: 09/696,600

(22) Filed: Oct. 25, 2000

Related U.S. Application Data

(63) Continuation of application No. 09/208,349, filed on Dec. 9, 1998, now abandoned.

(60) Provisional application No. 60/069,057, filed on Dec. 10, 1997.

(51) Int. Cl.
C12N 15/82  (2006.01)
C12N 15/90  (2006.01)
C12N 15/87  (2006.01)

(52) U.S. Cl. .................... 800/278; 435/320.1; 800/288

(58) Field of Classification Search ............... 435/69.1, 435/320.1, 410–416, 419, 468; 800/278, 800/287, 295, 298, 301, 302, 309, 312, 317.4, 800/320.1, 288
See application file for complete search history.

(56) References Cited

U.S. PATENT DOCUMENTS

| | | | | |
|---|---|---|---|---|
| 5,013,658 A | 5/1991 | Dooner et al. | ............... | 435/419 |
| 5,478,369 A | 12/1995 | Albertsen et al. | ........... | 800/278 |
| 5,482,852 A | 1/1996 | Yoder et al. | ................. | 435/468 |
| 5,527,695 A | 6/1996 | Hodges et al. | ............... | 435/468 |
| 5,658,772 A | 8/1997 | Odell et al. | ................. | 435/468 |

OTHER PUBLICATIONS

Shalev et al., Genetics, 1997, vol. 146, pp. 1143-1154.*
Swoboda et al., EMBO J., 1994, vol. 13, paes 484-489.*
Holtorf et al., Plant Mol. Biol., 1995, vol. 29, pp. 637-646.*
Fromm et al., Biotechnology, 1990, vol. 8, pp. 833-839.*
Athma, P., et al., "Ac Induces Homologous Recombination at the Maize P Locus", *Genetics* 128:163-173 (May, 1991).
Boeke, ed. Berg & Howe, *Mobile DNA* 335 (Am. Soc. Microbio. 1989) Chapter 13 (pp. 335-374).
Busseau, I., et al., "I elements of *Drosophila melanogaster* generate specific chromosomal rearrangements during transposition", *Mol. Gen Genet* 1989 218:222-228.
Chiurazzi, M., "Enhancement of Somatic Intrachromosomal Homologous Recombination in Arabidopsis by the HO Endonuclease", *The Plant Cell*, 8:2057-2066 (Nov. 1996).
Davis, P., et al., "Asymmetrical pairings of transposons in and proximal to the white locus of *Drosophila* account for four classes of regularly occurring exchange products", *Proc Natl Acad Sci USA* 84:174-178 (Jan. 1987).
Dooner, et al., "The frequency of transposition of the maize element *Activator* not affects by an adjacent deletion", *Mol. Gen. Genet.* (1988) 211:485:491.
Döring, H., "Transposable Element Ds at the *shrunken* Locus in *Zea mays*", *Mol Gen Genet* 184:377-380 (1981).
Hain, R., "Disease resistance results from foreign phytoalexin expression in a novel plant", *Nature* 361:153-156 (1993).
Kohler, U, "The maize GapC4 promoter confers anaerobic reporter gene expression and shows homology to the maize anthocyanin regulartory locus C1", *Plant Molecular Biology*, 29:1293-1298, 1995.
Lowe, B., Active *Mutator* Elements Suppress the Knotted Phenotype and Increase Recombination at the *Kn1-O* Tandem Duplication, *Genetics* 143:813-822 (Nov. 1992).
Martin, et al., "Large-Scale Chromosomal Restructuring is induced by the Transposable Element Tam3 at the *nivea* Locus of *Antirrhinum majus*", *Genetics* 119:171-184 (May 1988).
McClintock, B., "Mutations in Maize and Chromosomal Aberrations in Neurospora", 53 Washington Year Book 254 (1954) pp. 298-304.
Odell, J., "Site-directed recombination in the genome of transgenic tobacco", *Mol. Gen Genet* 223:369-378 (1990).
Szostak, J., "The Double-Stranded-Break Repair Model for Recombination", *Cell* , 33:25-35 (1983).
Taylor, L., "A deletion adjacent to the maize transposable element Mu-1 accompanies loss of *Adh 1* expression", *The EMBO Journal*, 4:869-876 (1985).

* cited by examiner

*Primary Examiner*—Ashwin Mehta
(74) *Attorney, Agent, or Firm*—McKee, Voorhees & Sease, P.L.C.

(57) ABSTRACT

The present invention is drawn to methods and materials to induce homologous recombination in a plant, comprising introducing a recombination construct to a plant and making available to the plant a transposase, so as to induce recombination. Preferably, the recombination construct and transposase are from maize.

25 Claims, 2 Drawing Sheets

PCR primer pairs:
Lane 1 - PCR negative control
Lanes 2 & 7 - PCR primer pair GUS1+H3
Lanes 3 & 8 - PCR primer pair H2+Ds(-)
Lanes 4 & 9 - PCR primer pair H1+H2
Lanes 5 & 10 - PCR primer pair 35S+(U)S
Lanes 6 & 11 - Ac primer pair

METHOD AND MATERIALS TO INDUCE RECOMBINATION IN PLANTS

This a Continuation application of application Ser. No. 09/208,349 filed Dec. 9, 1998, now abandoned. This application claims priority to Provisional Patent Application Ser. No. 60/069,057 filed Dec. 10, 1997.

BACKGROUND OF THE INVENTION

Field of the Invention

Transposons, or transposable elements, are mobile genetic elements characterized by their ability to move in and out of their host genome in a manner similar to bacteriophages. However, unlike bacteriophages, transposable elements are unable to move from host to host, since they lack the structural features necessary to package and deliver the nucleic acid.

Transposable elements have been shown to induce recombination in yeast (Boeke, ed. Berg & Howe, *Mobile DNA* 335 (Am. Soc. Microbio. 1989); *drosophila* (Davis et al., 84 *PNAS* 174 (1987) and Busseau et al., 218 *Mol. Gen. Genet.* 222 (1989)) and plants (Martin et al., 119 *Genetics* 171 (1988), McClintock, 53 *Washington Year Book* 254 (1954), Doring et al., 184 *Mol. Gen. Genet.* 377 (1981), Taylor and Walbot, 4 *EMBO J.* (1985), Dooner et al., 211 *Mol. Gen. Genet.* 485 (1988); Lowe et al., 132 *Genetics* 813 (1992) and Athma and Peterson, 128 *Genetics* 163 (1991)). The recombinations resulted in deletions, duplications and other rearrangements. These studies were limited to observations of natural phenomenon in the organisms, and did not involve in situ recombination of non-self constructs.

Human manipulation of transposons has been limited, until the present invention, to insertion and excision of transposons, with or without accompanying nucleic acid. For example, U.S. Pat. No. 5,482,852 to Yoder et al. describes a technique for inserting an expression-cassette-containing transposon into plant cells, selecting cells which contain the transposon, and subsequently crossing the plant so as to remove the transposon sequences, but not the expression cassette. U.S. Pat. No. 5,013,658 to Dooner describes a method to use selectable markers in transposons as tags for genetic studies. U.S. Pat. No. 5,478,369 to Albertson describes a male-fertility mediating gene which was cloned through the use of the Ac (maize) transposon.

Human manipulation of recombination has been limited, until the present invention, to non-transposon related methods. U.S. Pat. No. 5,527,695 to Hodges et al. describes the use of a recombinase enzyme to induce recombination in situ of a construct with homologous direct repeats. U.S. Pat. No. 5,658,772 to Odell et al. describes a similar method, but the crossover site and the recombinase enzyme are more defined (lox and Cre, respectively). In Arabidopsis, generation of double strand breaks by HO endonuclease increased the frequency of somatic intrachromasomal homologous recombination by about 10 fold. Chiurazzi et al., 8 *Plant Cell* 2057 (1996). Moreover, double strand breaks are known to initiate recombination in fungi. Szostak et al., 33 *Cell* 25 (1983).

Citation of the above documents is not intended as an admission that any of the foregoing is pertinent prior art. All statements as to the date or representation as to the contents of these documents is based on subjective characterization of information available to the applicant at the time of writing, and does not constitute an admission as to the accuracy of the dates or contents of these documents.

SUMMARY OF THE INVENTION

It is therefore an object of the present invention to provide a molecular system useful to induce recombination in plants.

It is a further object to provide a molecular system useful to increase the frequency of recombination events in plants over the naturally-occurring frequency.

It is yet another object to provide a molecular system for introducing part or parts of a construct into a plant cell and subsequently causing the part or parts to recombine.

It is yet another object to provide a molecular system for inducing recombination in plants at particular times, in inserted sequences.

In all of the above embodiments, it is an object to provide a molecular system which is useful to direct timing of transcription of constructs and timing of expression of construct products.

In another embodiment, it is an object to provide a method to affect the timing of complementary nucleic acid production in a plant cell.

It is another object to provide a molecular system which is useful to affect naturally-occurring sequences.

It is also an object of the invention to provide an in situ molecular system for constructing fusion protein-encoding sequences as well as expression of the fusion protein encoded.

It is a further object to provide a molecular system for making directed change(s) in a construct after it has been integrated into the genome of a plant.

In all of these embodiments, it is an object to provide compositions useful to induce homologous recombination in plants, including constructs, plasmids, viruses, cells and plants.

DETAILED DESCRIPTION OF THE INVENTION

Figure 1:
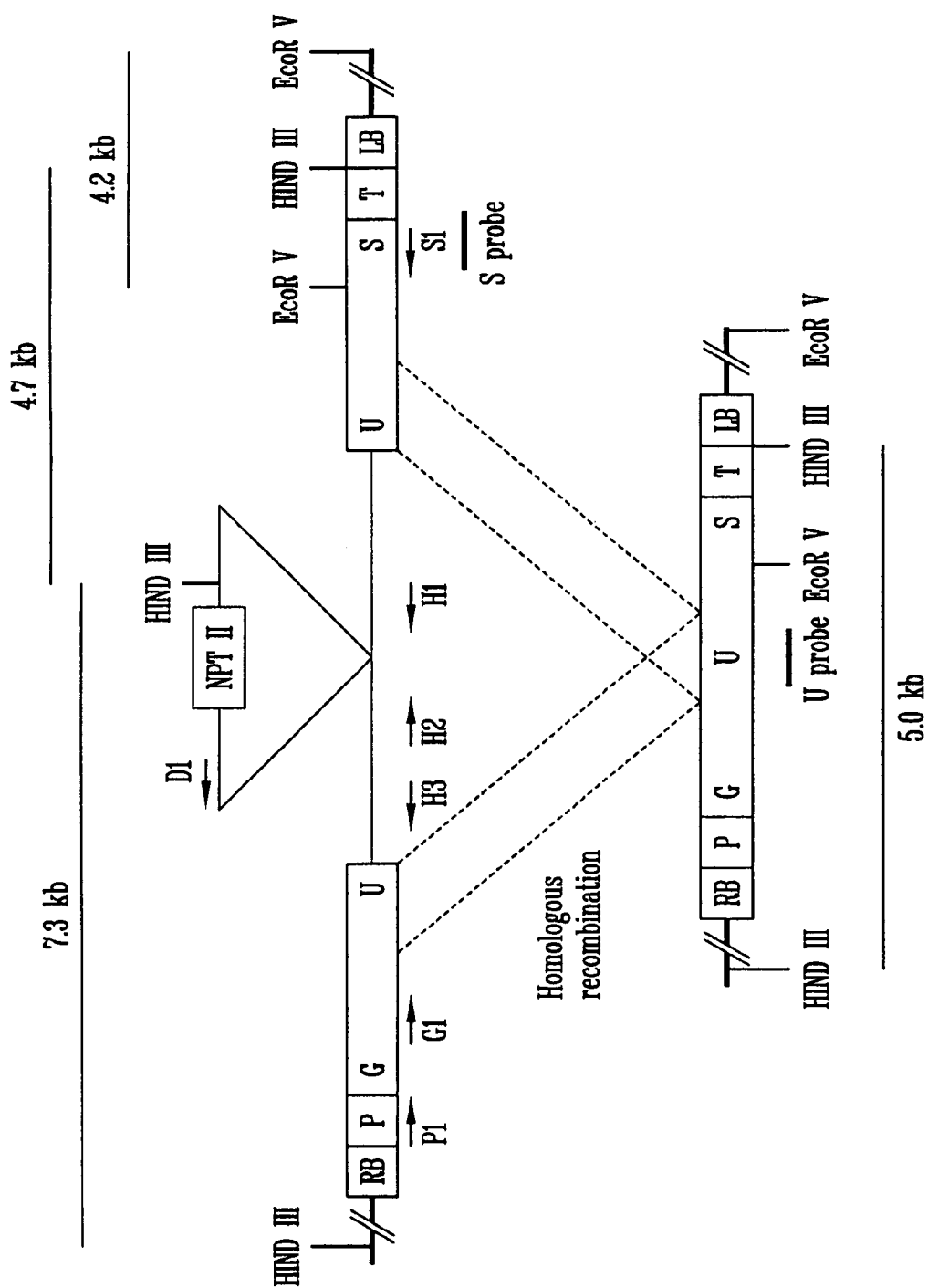
FIG. 1 is schematic of a GU-Ds-US construct.
Figure 2A:
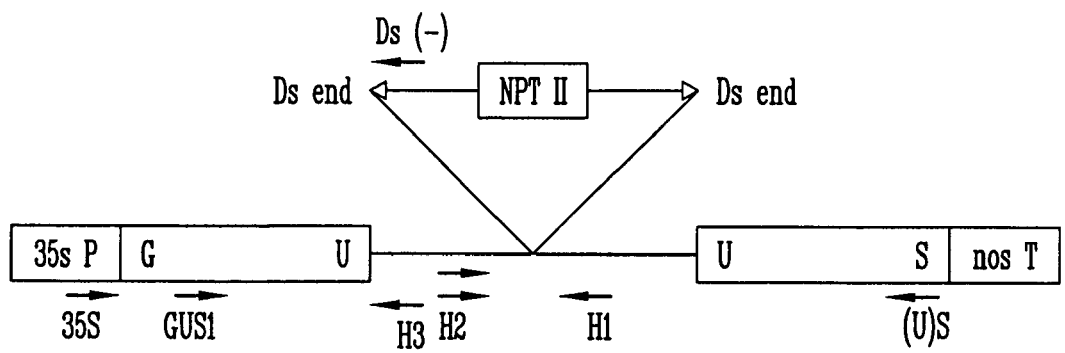
FIG. 2A is a map of a GU-Ds-US construct, showing primer construct location
Figure 2B:
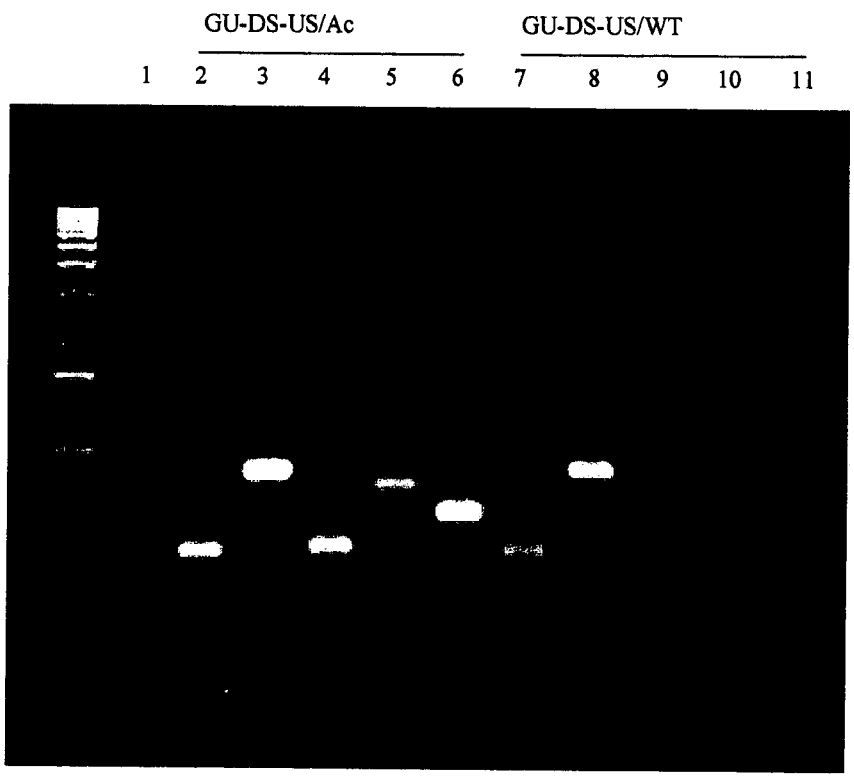
FIG. 2B is an agarose gel showing PCR amplification products for certain pairs of primers.

The present invention is directed to the unexpected finding that overlapping foreign gene sequences containing a maize Ds element can be induced to undergo homologous recombination upon introduction of the maize Ac transposase. The studies in this regard were in the *Arabidopsis* plant, using the overlapping, but incomplete, fragments of the GUS gene (a bacterial gene) to flank a Ds element. The Ac transposase was shown to induce recombination of the foreign GUS gene fragments to produce a functional GUS gene. The frequency of homologous recombination was increased by over 1000 fold over that which is normally seen in nature. This high recombination rate suggests that the action of the Ac transposase may not be explained solely by induction of a double strand break, but probably reflects a heretofore unknown effect of the Ac transposase.

Previous to the present invention, transposons were thought to be useful as passive vectors for inserting and deleting foreign constructs into and out of cells. In the present invention, transposons are viewed in a completely different light; transposons, or their parts, can now be considered active tools for recombining foreign constructs in situ. Moreover, the Ac transposase can now be used to regulate the timing of functional transcripts and construct products without the need for inducible promoters or enhancers at the site of insertion.

Transposon-induced recombination can be useful to enhance the frequency of certain homology-dependent gene manipulations in plants. The *Arabidopsis* and maize genomes are currently being saturated with Ac/Ds insertions, and it is possible to induce recombination between endogenous sequence duplications that carry Ac/Ds insertions. Such recombination events can generate interstitial deletions that could simplify the analysis of multicopy gene clusters such as are frequently associated with disease resistance genes. Transposon-induced recombination can also be used to delete undesirable sequences from integrated transgenes, or to delete multiple transgene copies that are commonly generated in many transformation protocols.

Therefore, one broad aspect of the present invention is drawn to methods to induce homologous recombination in a plant, comprising introducing a recombination construct to a plant and making available to the plant a transposase, so as to induce recombination. Preferably, the recombination construct and transposase are from maize.

For example, the above aspect can be implemented in the following manners:

A. The recombination construct may be a simple Ds element which is transformed into a plant and inserted between known direct repeats in the genome.

B. The recombination construct may be a Ds element flanked by direct repeats. In one such embodiment, this construct would enable disruption of a gene and subsequent regeneration of function via homologous recombination.

C. The recombination construct may be a Ds element flanked by overlapping sequences having homologous regions. In one such embodiment, the sequences, when recombined, may encode ie. a gene, coding region or fusion protein.

D. The recombination construct may be a Ds element-gene construct which is flanked by direct repeats. In one such embodiment, the direct repeats can be nonsense repeats, and in another, the direct repeats can encode a gene product when recombined.

All of the above recombination constructs may optionally contain a selection marker or other sequences.

E. The transposase can exist as a natural product of the plant, and the construct can be introduced to the plant which contains the transposase.

F. The transposase can be cotransformed, or present on the recombination construct, with or without an inducible promoter.

G. The transposase can be provided by way of a cross between a recombination construct-containing plant and a transposase-containing plant.

In all of the above aspects, the recombination construct and/or the transposase may be transiently or stably transformed into the plant. In this respect, the recombination construct or transposase genes may or may not be integrated into the genome of the plant. In all of the above aspects, the orientation of the Ds element and/or construct is not essential; either can be oriented in any manner. However, in all of the above aspects, it is preferable that the Ds element is between the direct repeats (for example, as in FIG. 1), although it is possible to induce recombination when the Ds element is within the direct repeats.

By "transposase" it is meant any plant transposase, ie. an enzyme that can induce homologous recombination in the presence of a Ds or Ac element.

By "Ac element" it is meant that which is typically understood in the art as the definition: any form of maize Ac, including any isolate or any allelic variant or homologue thereof.

By "plant" it is meant one or more plant seed, plant embryo, plant part or whole plant. The plant may be a monocot or dicot, man-made or naturally-occurring.

By "recombination construct" it is meant a full or partial (recombination-inducing) isolated Ds element either in conjunction with, or without, other isolated nucleic acid sequences, such as, for example, a regulatory sequence (promoter, enhancer, terminator, etc.), an isolated full gene sequence, an isolated coding region, or an isolated partial natural or artificial sequence. Therefore, an Ac element with altered transposase function is within this definition.

By "overlapping sequences having homologous regions" or "overlapping sequences having homologous sequences" it is meant that the entire sequence which encodes the construct product (or regulatory region) desired must be represented by the two fragments, and that some of the same internal sequences must exist on each of the two fragments so as to allow recombination of the fragments to produce a complete construct. The gene product need not be a naturally-occurring gene product, nor need encode an independently-functional gene product. It could, for example, encode a fusion protein or sub-unit of a functional complex. Additionally, it could encode a complementary transcript useful for inhibiting translation of mRNA. Lastly, the sequences could be nonsense sequences used simply for their ability to recombine.

By "proteins" it is meant any compounds which comprise amino acids, including peptides, polypeptides, fusion proteins, etc.

By "Ds element" it is meant not only the definition known in the art, ie. a transposon or part of a transposon without the sequence for a functional transposase, but also the instance where the element possesses a transposase coupled with a regulatory region which is post-insertion manipulatable. For instance, it is within the present definition of "Ds element" the instance where the element is an isolated natural transposon, with an inducible promotor inserted at the appropriate site upstream from the transposase, so as to allow human manipulation of the timing of transcription and expression of the transposase. However, the full transposon is not necessary. In other words, so long as the Ds element retains the ability to induce recombination, the presence or absence of sequences present in the naturally-occurring Ds element or transposon is not critical. "Ds element" includes the classic "dissociation"-type of element (ie, "state 1" and "state 2"), as well as the full gamut of more recently characterized Ds elements, ie. those with inverted repeats.

By "making available the transposase" it is meant that the transposase becomes available at levels to cause an increase in homologous recombination over that seen in the plant under normal conditions. In other words, the naturally-occurring Ac transposase, in the case of maize, could be caused to over-express, or a construct could be introduced which operably links an inducible promoter or enhancer to the Ac sequence. In all plants, the transposase can be introduced via co-transformation (on the same or separate vectors) with the recombination construct, or subsequent to the transformation of the recombination construct. In either case (co-transformation or subsequent transformation) the transposase can be linked operably to an inducible promoter or enhancer which would cause the gene product to be available in the cell at a pre-determined time. In some instances, it may be desirable to cause the transposase to be available as soon as the recombination construct has been introduced, and in such case, it may be desirable to introduce the vector containing the transposase prior to introduction of the recombination construct, so that the enzyme can be active as soon as possible subsequent to the introduction of the recombination construct. In other instances, it may be desirable to provide the transposase in such a manner that the enzyme would be induced upon a certain environmental or internal occurrence. Another means for subsequently making available the Ac transposase is as is described in the Examples: crossing a plant transformed with the recombination construct with a plant expressing the transposase. The transposase in this instance can be naturally-occurring or provided via genetic engineering.

By "introducing" it is meant any means of transferring nucleic acid into the cell. For example, any of the following known means can be used: infective, vector-containing bacterial strains (such as *Agrobacterium rhizogenes* and *Agrobacterium tumefaciens*) according to ie. Zambryski, 43 *Ann. Rev. Pl. Physiol. Pl. Mol. Biol.* 465 (1992); pollen-tube transformation [Zhon-xun et al., 6 *Plant Molec. Bio.* 165 (1988)]; direct transformation of germinating seeds [Toepfer et al., 1 *Plant Cell* 133 (1989)]; polyethylene glycol or electroporation transformation [Christou et al., 84 *Proc. Nat. Acad. Sci.* 3662 (1987)]; and biolistic processes [Yang & Cristou, *Particle Bombardment Technology for Gene Transfer* (1994)].

The transformed cells may be induced to form transformed plants via organogenesis or embryogenesis, according to the procedures of Dixon *Plant Cell Culture: A Practical Approach* (IRL Press, Oxford 1987).

Any seed, embryo, plant or plant part is amenable to the present techniques. Of course, the agronomically-significant seeds, embryos, plants or plant parts are preferred. Soybean, maize, sugar cane, beet, tobacco, wheat, barley, poppy, rape, sunflower, alfalfa, sorghum, rose, carnation, gerbera, carrot, tomato, lettuce, chicory, pepper, melon and cabbage are among the preferred seeds, embryos, plants or plant parts. Particularly preferred are: soybean, tobacco and maize seeds, embryos, plants or plant parts. However, *Arabidopsis* seeds, embryos, plants or plant parts are also preferred, since it is an excellent system for study of plant genetics.

In the case of a recombination construct containing the Ds element and other isolated nucleic acid sequences, the nucleic acid sequences can be any that are useful in plant genetics. Preferred are those genes or sequences which are agronomically significant. For example, genes encoding male sterility, foreign organism resistance (viruses or bacteria), including genes which produce bacterial endotoxins, such as *bacillus thurigiensis* endotoxin, genes involved in specific biosynthetic pathways (eg. in fruit ripening, oil or pigment biosynthesis, seed formation, or starch metabolism) or genes involved in environmental tolerance (eg. salt tolerance, drought tolerance, or tolerance to anaerobic conditions). The choice of gene or sequence induced to recombine in the present invention is not limited. Examples of genes and how to obtain them are available through reference articles, books and supply catalogs, such as *The Sourcebook* (1-800-551-5291). Sambrook et al., *Molecular Cloning. A Laboratory Manual* (Cold Spring Harbor Laboratory Press, 1989) and Weising et al., 22 *Ann Rev. Gen.* 421 (1988) also have pertinent information.

Plants which have undergone induced homologous recombination can be identified by Southern blot analysis, by identification of the particular gene product expressed (marker rescue) or deleted (marker loss) through recombination, or by the methods described in U.S. Pat. No. 5,482,852 to Yoder et al., (PCR, regain of function) which patent is herein incorporated by reference. These techniques are well-known in the art.

Where and when the sequences are inserted can also contribute to the overall desirability of the end product. For example, it may be desirable to select for seeds, embryos, or plant parts (all within the definition of "plants") which have incorporated the sequences in strategically-beneficial locations. In one instance, it may be desirable to select a plant which has incorporated a sequence so as to cause a disruption or other alteration of a coding or regulatory region of a genomic gene sequence. This is within skill of the art, and considered part of the present invention. Moreover, it may be desirable to introduce the recombination construct and/or transposase gene to an undifferentiated cell or callus of cells, so that the entire plant contains the constructs and/or genes.

In the case of a recombination construct containing direct repeats, the direct repeats may be any length which allows homologous recombination to be induced upon introduction of the transposase. In general, the larger the length of the direct repeats the more likely it is that homologous recombination will be successful, although at certain long lengths (greater than 10 kilobases, perhaps) the relative increase over that seen with shorter lengths may be diminishing. In one embodiment of the present invention, the direct repeats are from 300 base pairs to 10 kilobase pairs in length, although it is possible to have fewer or more, depending on the particular application desired. Preferably, the direct repeats are 600 base pairs to 6 kilo base pairs in length.

In the case of a recombination construct containing direct repeats, the distance between the direct repeats (not including the length of the direct repeats themselves) may be any length which allows homologous recombination to be induced upon introduction of the transposase. In one embodiment of the present invention, the distance between the direct repeats is from approximately 25 base pairs to approximately 15 kilo base pairs. Preferably, the distance between the direct repeats is 6 kilobases to 12 kilobases, and includes an approximately 4.6 kilobase sequence of a Ds element.

Therefore, there are provided methods to induce transcription and/or translation of a gene in a plant comprising introducing to the plant a Ds element containing overlapping sequences having homologous regions, which sequences, when homologously recombined, result in a gene and subsequently making available to the plant the transposase, so as to induce homologous recombination and subsequent transcription and translation of said gene. Preferred plants, genes and sequences are those described previously.

Also provided are methods to disrupt or otherwise alter a naturally-occurring sequence (including genes) in plants, comprising introducing to the plant a recombination construct having direct repeats useful for subsequent removal of the recombination construct via homologous recombination. Preferred plants, genes and sequences are those described previously. Transgenic knockout plants or plants with specific genomic changes can be obtained by these methods.

Moreover, methods to construct a fusion protein sequence in plants, comprising introducing to the plant a recombination construct having overlapping sequences having homologous regions, which sequences, when homologously recombined, result in a fusion protein sequence, and making available to the plant a transposase, so as to cause recombination and construction of a fusion protein sequence. Preferred plants, genes and sequence are those described previously.

Also provided is a method to induce complementary nucleic acid sequence production in plants, comprising introducing to the plant a recombination construct having overlapping sequences having homologous regions, which sequences, when homologously recombined, result in complementary nucleic acid sequences, and making available to the plant a transposase, so as to cause recombination and production of said complementary nucleic acid sequences. Preferred plants and genes are those described previously.

The present invention also provides materials useful in the present invention.

In particular, plants comprising a recombination construct are provided. Such plants are those which have been previously described, although maize and *arabidopsis* are preferred plants herein provided. The presently-identified plants can inherently possess the transposase activity, or have artificially modified transposase activity. Plants wherein the transposase activity is provided via an inducible promoter is preferred, although plants which are crosses between a Ds-construct-transformed plant and a plant in which transposase is naturally occurring is also preferred.

Vector comprising the transposase and recombination construct are therefore also provided by the present invention. Vectors with either an early or late promoter in conjunction with a transposase and/or a recombination construct are particularly provided. Vectors may be from bacterial, viral or artificial origin. Vectors of the present invention optionally comprise the following promoters useful in early expression of plant sequences:

Ogs4B (Tsuchiya et al., 36 Plant Cell Physiology 487 (1994)

TA29 (Koltunow et al., 2 Plant Cell 1201 (1990)

A3 & A9 (Paul et al., 19 Plant Molecular Biology 611 (1992)

In order to then constitutively express the sequences described above, the vector optionally contains, for example, a 35S promoter.

Vectors may be obtained from various commercial sources, including Clontech Laboratories, Inc. (Palo Alto, Calif.), Stratagene (La Jolla, Calif.), Invitrogen (Carlsbad, Calif.), New England Biolabs (Beverly, Mass.) and Promega (Madison, Wis.).

Genes can be obtained through catalogues such as *The Sourcebook* (1-800-551-5291 or conventional methods as in Sambrook et al., *Molecular Cloning. A Laboratory Manual* (Cold Spring Harbor Laboratory Press, 1989).

The Ac transposase sequence can be obtained by Genbank Accession Number: X01380, and either cloned according to Sambrook (above) or obtained as has been previously described.

A Ds element can be obtained by using the Ac element (above), or portion thereof as a probe to detect a Ds element or Ac element. If the element retrieved is an Ac element, internal sequences can be removed so as to eliminate transposase function. Alternatively, because the terminal inverted repeats of Ds (and Ac) elements are conserved, and the subterminal sequences are somewhat conserved, primers can be designed and used for PCR amplification of a Ds element or Ac element. Again, if an Ac element is amplified, internal sequences can be removed so as to eliminate transposase function, so as to obtain a Ds element. Of course, an Ac element can also be modified via insertion of an -inducible promoter designed to drive the transposase. Oligonucleotide primers that can be used to PCR amplify Ac or Ds elements from maize are 5'-CAGGGATGAAAGTAG-3' (SEQ ID NO 1, from the 5' end of Ac terminal sequence) and 5'-TAGG-GATGAAAACGG-3' (SEQ ID NO 2, from the 3' end of Ac terminal sequence). The methods for conducting these types of molecular manipulations are well-known in the art, and are described in detail in Sambrook et al., *Molecular Cloning. A Laboratory Manual* (Cold Spring Harbor Laboratory Press, 1989) and Ausubel et al., *Current Protocols in Molecular Biology* (Greene Publishing Associates, Inc., 1993). Moreover, Ds elements can be obtained from researchers willing to send samples, or from other publicly-available sources. For instance, the *Arabidopsis* Biological Resource Center, Ohio State University, 309 B&Z Building, 1735 Neil Avenue, Columbus, Ohio 43210, (Phone: 614-292-9371) will provide plasmid pWS31 (stock number CD3-125), containing DsE, and plasmid pWS32 (stock number CD3-126) containing DsG. Other Ds elements can be obtained from the American Type Culture Collection, Rockville, Md. (800) 638-6597.

Direct repeats can be synthesized de novo, or retrieved from plasmid preparations carrying the desired sequences. For instance, if overlapping sequences having homologous regions are desired, a plasmid preparation can be divided into two batches, with one batch subjected to a restriction enzyme digestion which cleaves at one site, and the other batch subjected to a restriction enzyme digestion which cleaves at a different, overlap-causing site. The methods for conducting these types of molecular manipulations are well-known in the art, and are described in detail in Sambrook et al., *Molecular Cloning. A Laboratory Manual* (Cold Spring Harbor Laboratory Press, 1989) and Ausubel et al., *Current Protocols in Molecular Biology* (Greene Publishing Associates, Inc., 1993).

Recombination constructs can be made using the starting materials above or with additional materials, using methods well-known in the art. In general, the sequences can be manipulated to have ligase-compatible ends, and incubated with ligase to generate full constructs. For example, restriction enzymes can be chosen on the basis of their ability to cut at an acceptable site in both sequence to be ligated, or a linker may be added to convert the sequence end(s) to ones that are compatible. The methods for conducting these types of molecular manipulations are well-known in the art, and are described in detail in Sambrook et al., *Molecular Cloning. A Laboratory Manual* (Cold Spring Harbor Laboratory Press, 1989) and Ausubel et al., *Current Protocols in Molecular Biology* (Greene Publishing Associates, Inc., 1993). The methods described herein according to Tinland et al., 91 *Proc. Natl. Acad. Sci. USA* 8000 (1994) can also be used.

Constructs with Ac transposase can be made according to the methods described in Calvi et al., 66 *Cell* 465 (1991); Long et al., 241 *Mol. Gen. Genet.* 627 (1993); and Honma et al., 90 *Proc. Natl. Acad. Sci.* 6242 (1993).

The present invention also includes compositions of matter which can be induced to undergo homologous recombination upon introduction of a maize transposase comprising a maize recombination construct having proximal direct repeat sequences. By "proximal" it is meant that the Ds element is flanked, either with or without intervening sequences, by the direct repeats. That is, so long as the Ds element is internal to at least two direct repeats, such that at least one direct repeat is at either end of the Ds element, the direct repeat sequences are "proximal". Other sequences can exist between the direct repeats as well. The direct repeats can be artificial or naturally-occurring, isolated sequences. The recombination construct can be made according to the methods detailed previously.

Also provided are compositions of matter which can be induced to undergo homologous recombination upon introduction of a maize transposase comprising a maize recombination construct having proximal direct repeat sequences as part of a vector. The vector can be any nucleic acid sequence or other carrier (ie. liposomes) useful for transferring the recombination construct during molecular manipulations. These compositions can be made according to the methods detailed previously.

Also provided are compositions of matter which can be induced to undergo homologous recombination upon introduction of a maize transposase comprising a maize recombination construct having proximal direct repeat sequences in a plant. These compositions can be made using any plants, especially the plants disclosed herein as useful the present invention. Compositions as described, which further comprise a transposase gene under control of an inducible promoter, or a gene internal to said direct repeat sequences, or wherein the direct repeat sequences are in the form of overlapping sequences having homologous regions are preferred. These compositions can be made according to the methods detailed previously.

The following are examples are not intended to limit the scope of the present invention as described and claimed. They are simply for the purpose of illustration.

EXAMPLES

Example 1

Preparation of Nucleic Acids

A Ds element (courtesy of V. Sundaresan) was inserted between two partially overlapping non-functional segments of the (-glucuronidase gene5 (GUS; courtesy of H. Puchta) to generate a binary plant transformation vector termed GU-Ds-US (FIG. 1). The sequences were prepared according to Tinland et al., 91 *Proc. Natl. Acad. Sci. USA* 8000 (1994) and the plasmid containing the sequences was called "plasmid GU.US." The homologous direct repeat sequences are 618 bp in length, and the distance between them is 6.3 kb including the 4.6 kb Ds element.

In particular, plasmid pWS31 (described in Sundaresan et al., 9 *Genes Dev.* 1797 (1995)) with a Ds element was cut with Sal I and religated to remove the GUS gene in pWS31 (according to Sambrook et al., *Molecular Cloning. A Laboratory Manual* (Cold Spring Harbor Laboratory Press, 1989)), and the new plasmid was named pWS31Y. SacI was used to digest pWS31Y, and the 4.8 kb Ds fragment was purified via an 0.8% agarose gel using Promega Wizard DNA Clean-up System according to Ausubel et al., *Current Protocols in Molecular Biology* (Greene Publishing Associates, Inc., 1993).

Plasmid GU.US was digested with PstI restriction enzyme and Promega Wizard DNA Clean-Up System was used to purify the DNA, as above. A PstI-SacI adaptor was designed, and subsequently synthesized by ISU DNA Synthesis Facility, using standard synthesis procedures.

The PstI cut GU.US, the 4.8 kb Ds fragment and the PstI-SacI adaptor were ligated together, and subsequently transformed into *E. coli*. A plasmid GU-Ds-US was obtained. Sequence from the cloning junction confirmed proper sequence configuration for further studies.

Example 2

Transformation of Plants

The electroporation method described in Ausubel et al., *Current Protocols in Molecular Biology* (Greene Publishing Associates, Inc., 1993) was used to transform GU-Ds-US into *Agrobacterium* strain ASE. The vacuum infiltration method was used to transform *Agrobacterium* into *Arabidopsis*, Columbia ectotype. Seeds were selected on the plate with 30 ug/ml kanamycin. After one week, transformants were transferred from selection plates to soil. Plants were grown in growth chamber under conditions of 16 hours light/8 hours dark at 20–22 centigrade. These procedures were according to Ellis et al., 316 *C. R. Acad. Sci. Paris* 1194 (1993); Bent et al. 265 *Science* 1856 (1994) and Koncz et al., 204 *Mol. Gen. Genet.* 383 (1986).

Example 3

Growth of Plants/Identification of Recombination

The T1 seeds were harvested from the plants transformed according to Example 2. From each independent transformant, 17 seeds were planted. Southern hybridization was used to check the insertion number of the GU-Ds-US construct to get the single insertion transformant. Then, the T2 seeds were harvested from single insertion lines and the seeds were put on selection plates to obtain homozygous lines of the transgene. The plants with the single insertion and the plants homozygous for the transgene were used as the starter lines.

The starter lines and lines with stable Ac transposase (obtained from *Arabidopsis* Stock Center (CS8045, CS8537, CS8538) were planted. The starter lines were used as the pollen donor and the stable Ac lines as the pollen receptor in crosses. At the same time, the starter line pollen was crossed to wild-type (WT) *Arabidopsis* (No-O and Landsberg) as control.

F1 heterozygous seeds (GU-Ds-US/−, Ac−and GU-Ds-US/−) were planted. When the plants were at full rosette stage, the whole plant was used for X-Glu staining according to Jefferson, 5 *Plant. Mol. Biol. Rep.* 387 (1987) and Swoboda et al., 13 *EMBO J.* 484 (1994).

Simple excision of Ds was predicted to not restore an intact GUS gene, whereas homologous recombination between the partially-duplicated GUS segments would give a functional GUS gene detectable by staining. Comparisons between sibling plants with and without Ac transposase indicates the degree to which homologous recombination is stimulated by Ac transposase over the level of spontaneous recombination. The results show that Ac induces recombination of the GU-Ds US substrate at a surprisingly high frequency in Arabidopsis.

As shown in Table 1, plants in the control group (genotype GU-Ds-US/+, no Ac) had zero or few blue sectors (average of 0.6 blue sectors per plant), whereas plants in the experimental group commonly had hundreds of blue sectors (average of 700 blue sectors per plant). These results were obtained from three independently transformed GU-Ds-US lines (DsI5, DsI6, DsII7), in crosses with three different lines expressing Ac transposase (CS8045, CS8537, CS8538). Based on the average numbers of blue sectors, the calculated spontaneous recombination frequency of the GU-Ds-US transgene in the absence of Ac transposase is approximately $1.99 \times 10^{-7}$ to $5.40 \times 10^{-8}$ events/genome3. This frequency is similar to that reported by others for spontaneous recombination of a similar GU.US transgene3,7,8. In the presence of the sAc transposase source, the average recombination frequency is increased >1,000 fold.

The data from the above experiment is as follows:

TABLE 1

Frequency of recombination in GU-Ds-US-transformed Arabidopsis plants, with and without available Ac transposase. Recombination is shown by blue spots (in CS 8045 × Ds I 5).

| Type of Plant | Number of Plants | Total Number of Blue Spots |
|---|---|---|
| Control: Gu-Ds-US | 9 | 3 |
| Experimental: GU-Ds-US + Transposase | 10 | 3,310 |

TABLE 2

Frequency of recombination in GU-Ds-US-transformed Arabidopsis plant parts in the presence of Ac transposase. Recombination is shown by blue spots per part (in CS 8045 × Ds I 5).

| Plant | Cotyledon (parts/plant) | Leaf (parts/plant) | Stem | Root | Total |
|---|---|---|---|---|---|
| 1 | 15 (2) | 348 (9) | 9 | 43 | 415 |
| 2 | 33 (2) | 18 (8) | 4 | 16 | 71 |
| 3 | 50 (2) | 419 (10) | 5 | 62 | 536 |
| 4 | 17 (2) | 298 (10) | 0 | 59 | 374 |
| 5 | 22 (2) | 397 (10) | 0 | 57 | 476 |
| 6 | 21 (2) | 90 (10) | 0 | 63 | 174 |
| 7 | 20 (2) | 259 (9) | 6 | 64 | 349 |
| 8 | 35 (2) | 222 (10) | 5 | 23 | 285 |
| 9 | 5 (1) | 169 (7) | 2 | 25 | 201 |
| 10 | 61 (2) | 324 (7) | 8 | 36 | 429 |

Example 4

PCR and Southern Confirmation of Recombination Construct Recombination

Genomic DNA samples were amplified by PCR for 35 cycles as follows: denaturation at 94° C. for 30 sec; annealing at 57° C. for 30 sec; elongation for 1 min at 72° C. for 35 cycles. PCR products were cloned into pT7Blue T-vector (Novagen) and sequenced at the Iowa State University Nucleic Acid Facility, Ames, Iowa. Probe preparations and Southern blot hybridizations were performed as described.

The structure of the GU-Ds-US transgene in the presence or absence of the Ac transposase source (sAc) using PCR amplification of genomic DNA was determined. A band predicted to arise from the restored GUS gene was obtained using DNA from plants containing the GU-Ds-US construct together with sAc, but not from plants lacking sAc. The PCR band from the presumptive recombination product was sequenced and found to contain a precisely restored GUS gene. Similarly, a PCR product predicted to arise from Ds excision from the GU-Ds-US construct was found only in plants containing sAc, but not in plants lacking sAc. The sequence of the presumptive Ds excision product showed that it contained a typical Ds excision footprint.

Among the progeny of the variegated GUS+ plants, was detected several plants with uniform GUS+ expression. To test for germinal transmission of a recombined GUS transgene, the genomic DNA from plants with uniform GUS expression by Southern hybridization was analyzed. Hybridization with a GUS-specific probe detected two bands (7.3 kb and 4.7 kb) in HindIII-digested DNA from a plant of genotype GU-Ds-US/−, sAc/−, whereas the GUS-specific probe detected only one band of 5.0 kb in DNA from two plants with uniform GUS expression. These results are expected from the generation of a single GUS coding sequence by recombination between the homologous regions of the GU-Ds-US construct. To verify that the recombinant GUS+ plants were derived from the original GU-Ds-US transformants, additional Southern hybridizations were performed using enzymes that cleave in the DNA flanking the transgene insertion. Genomic DNA from plants of genotype GU-Ds-US, sAc and the uniform GUS+ plants were digested with EcoRV and hybridized with a probe specific for the 3' end of the GU-Ds-US construct (FIG. 1). The probe hybridizes to the same 4,2 kb band in the GU-Ds-US progenitor plants and the uniform GUS+ plants. This result indicates that the two GUS+ plants could not have arisen by seed or pollen contamination, but did in fact originate by recombination of the GU-Ds-US transgene locus.

Although the present invention has been fully described herein, it is to be noted that various changes and modifications are apparent to those skilled in the art. Such changes and modifications are to be understood as included within the scope of the present invention as defined by the appended claims.

What is claimed is:

1. A method to induce homologous recombination between nucleotide sequences having overlapping regions within a recombination construct in a plant, wherein said recombination construct comprises a transposon flanked by said nucleotide sequences, comprising: introducing said recombination construct to the plant, and expressing a transposase within the plant to cause excision of said transposon, so as to induce homologous recombination between said nucleotide sequences within said recombination construct within said plant so that the recombined sequence encodes a protein.

2. The method of claim 1, wherein the recombination construct comprises a maize Ds element as the transposon and the transposase is of maize origin.

3. The method of claim 2, wherein the recombination construct further comprises direct repeats proximal to the Ds element.

4. The method of claim 2, wherein the plant in which recombination is induced is selected from the group consisting of: soybean; maize; sugar cane; beet; tobacco; wheat; barley; poppy; rape; sunflower; alfalfa; sorghum; rose; carnation; gerbera; carrot; tomato; lettuce; chicory; pepper; melon; *Arabidopsis*; and cabbage.

5. A method to construct a functional gene in plants, comprising generating two overlapping fragments of the gene, assembling a recombination construct comprising a maize Ds element and the overlapping fragments flanking the Ds element in such an order that a complete sequence is obtained when these fragments are homologously recombined, introducing said recombination construct into a plant, and making available a transposase to cause excision of the Ds element, whereby homologous recombination is induced upon excision of the Ds element, between the overlapping fragments within the recombination construct to produce a functional gene.

6. The method of claim 5, wherein the functional gene is selected from the group consisting of: genes useful for disease resistance; genes useful for male sterility; genes useful for environmental condition tolerance; genes useful for fruit ripening, oil or pigment biosynthesis, seed formation, and starch metabolism.

7. The method of claim 5, wherein the plant in which recombination is induced is selected from the group consisting of: soybean; maize; sugar cane; beet; tobacco; wheat; barley; poppy; rape; sunflower; alfalfa; sorghum; rose; carnation; gerbera; carrot; tomato; lettuce; chicory; pepper; melon; *Arabidopsis*; and cabbage.

8. A method to control expression of a gene in a plant comprising:

1) generating two overlapping fragments of the gene sequence comprising regulatory elements;

2) linking the overlapping fragments with a maize Ds element;

3) assembling a recombination construct comprising the overlapping fragments flanking the Ds element in such an order that a complete gene sequence is obtained when these fragments are homologously recombined;

4) introducing said recombination construct into a plant; and 5) making available a transposase to cause excision of the Ds element, whereby homologous recombination is induced, following excision of the Ds element, between the overlapping fragments within the recombination construct to produce a complete gene sequence which is capable of expressing a functional transcript in plants.

9. The method of claim 8, wherein the gene is selected from the group consisting of: genes useful for disease resistance; genes useful for male sterility; genes useful for environmental condition tolerance; genes useful for fruit ripening, oil or pigment biosynthesis, seed formation, and starch metabolism.

10. A method of claim 9, wherein the plant in which recombination is induced is selected from the group consisting of: soybean; maize; sugar cane; beet; tobacco; wheat; barley; poppy; rape; sunflower; alfalfa; sorghum; rose; carnation; gerbera; carrot; tomato; lettuce; chicory; pepper; melon; Arabidopsis; and cabbage.

11. A recombination construct comprising a DNA molecule which can be induced to undergo homologous recombination in the presence of a maize transposase, said recombination construct comprising two overlapping fragments of a gene and a maize Ds element, wherein the fragments flank the Ds element, wherein, in the presence of said transposase, the Ds element is excised and the overlapping fragments homologously recombine to form a functional gene.

12. A vector comprising the recombination construct of claim 11.

13. The recombination construct of claim 11, which further comprises a transposase gene under control of an inducible promoter.

14. The method of claim 3, wherein the recombination construct further comprises a gene internal to the direct repeats.

15. The method of claim 14, wherein the gene is selected from the group consisting of: genes useful for disease resistance; genes useful for male sterility; genes useful for environmental condition tolerance; genes useful for fruit ripening, oil or pigment biosynthesis, seed formation, and starch metabolism.

16. The method of claim 3, wherein the recombination construct further comprises a transposase gene under the control of an inducible promoter.

17. The method of claim 3, wherein the transposase is Ac.

18. The method of claim 16, wherein the transposase is Ac.

19. The method of claim 2, wherein the plant in which recombination is induced is maize.

20. The method of claim 2, wherein the maize Ds element comprises overlapping sequences having homologous regions, which sequences, when homologously combined, results in a functional gene.

21. The method of claim 1, wherein the plant is a monocot.

22. The method of claim 1, wherein the plant is a dicot.

23. The method of claim 20, wherein the gene is selected from the group consisting of: genes useful for disease resistance; genes useful for male sterility; genes useful for environmental condition tolerance; genes useful for fruit ripening, oil or pigment biosynthesis, seed formation, and starch metabolism.

24. The recombination construct of claim 13, wherein the transposase is Ac.

25. The recombination construct of claim 11, wherein the gene is selected from the group consisting of: genes useful for disease resistance; genes useful for male sterility; genes useful for environmental condition tolerance; genes useful fruit ripening, oil or pigment biosynthesis, seed formation, and starch metabolism.

* * * * *

SEQUENCE LISTING

<160> NUMBER OF SEQ ID NOS: 2

<210> SEQ ID NO 1
<211> LENGTH: 15
<212> TYPE: DNA
<213> ORGANISM: Zea mays

<400> SEQUENCE: 1
cagggatgaa agtag                                                   15

```
-continued

<210> SEQ ID NO 2
<211> LENGTH: 15
<212> TYPE: DNA
<213> ORGANISM: Zea mays

<400> SEQUENCE: 2
tagggatgaa aacgg                                                    15
```